United States Patent [19]
Roberts et al.

[11] Patent Number: 6,153,210
[45] Date of Patent: Nov. 28, 2000

[54] USE OF LOCALLY DELIVERED METAL IONS FOR TREATMENT OF PERIODONTAL DISEASE

[75] Inventors: F. Donald Roberts, Dover; Phillip M. Friden, Bedford; Peter Spacciapoli, Newbury; Eric Nelson, Waltham, all of Mass.

[73] Assignee: Periodontix, Inc., Watertown, Mass.

[21] Appl. No.: 08/911,413

[22] Filed: Aug. 14, 1997

[51] Int. Cl.[7] .............................. A61K 33/38; A61K 9/70; A61K 31/765; A61L 15/03
[52] U.S. Cl. .......................... 424/411; 424/422; 424/424; 424/425; 424/426; 424/435; 424/444; 424/445
[58] Field of Search ................................ 424/49–88, 411, 424/422, 424, 425, 426, 435, 444, 445

[56] References Cited

U.S. PATENT DOCUMENTS

Re. 33,093  10/1989  Schiraldi et al. .
3,337,405   8/1967  Netien .

(List continued on next page.)

FOREIGN PATENT DOCUMENTS

| 282292 | 6/1997 | Czech Rep. . |
|---|---|---|
| 0 241 179 | 3/1987 | European Pat. Off. . |
| 0508524A1 | 3/1992 | European Pat. Off. . |
| 6154030 | 6/1994 | Japan . |
| 7068109B | 6/1995 | Japan . |
| 2078559 | 5/1997 | Russian Federation . |
| 93/24103 | 12/1993 | WIPO . |
| WO 95/29664 | 11/1995 | WIPO . |
| WO 96/09808 | 4/1996 | WIPO . |
| WO 97/16212 | 5/1997 | WIPO . |

OTHER PUBLICATIONS

Merckinder Merck & Co. 11th Ed 8450 846484658 468 84738470 8475 Silver Compounds Topical Antiseptic, 84638462 84608 84578455 Silver Nitrate, etc. 8452 8451, 1989.

Fung et al. JL. Toxicology Clinical Toxicology 34(1): 119–126 Silver Products for Medical Indications: Risk–Benefit Ass; Silver Nitrate–Silver Sulfadiazine–Silver Protein (Mild)–Colloidal Silver (CSP), 1996.

Russell Progress in Medicinal Chemistry 31:351–370 Antimicrobial Activity and Action of Silver Silver Nitrate Silver Protein Silver Sulfadiazine Colloidal Silver, 1994.

Fung et al Journal of Toxicology Clinical Toxicology 34(1): 119–126 Silver Products for Medical Indications: Risk Benefit Assessment, 1996.

Rusch–Behrend et al Quintessence International 26(8): 553–557 Management of Diffuse Tissue Argyria Subsequent to Endodontic Therapy: Report of a Case, Aug. 1995.

Kirchoff Oral Surgery, Oral Medicine and Oral Pathology 32(4): 613–617 Localized Argyria After a Surgical Endodontic Procedure Report of a Case, Oct. 1971.

Chan Georgetown Dental Journal 62(2): 31–35 Amalgam Tattoos (Localized Argyria): A Review of the Literature, Jul. 1978.

Mack North Carolina Medical Journal 49(9): 451–452 Argyroc and Argyria Return With Us Now to Those Thrilling Days of Yesteryear, Sep. 1988.

Hudson et al Australian and New Zealand Jl. of Ophthalmology(4): 391–394 Argyrol Argyrosis and the Acquisition of Art, Nov. 1985.

(List continued on next page.)

*Primary Examiner*—Shep K. Rose
*Attorney, Agent, or Firm*—Clark & Elbing LLP

[57] ABSTRACT

Periodontal disease can be treated by the administration of metal ions, preferably silver ions, to the site where the microorganisms that cause this disease reside. Administration can be to periodontal pockets or adjacent to exposed tooth roots or alveolar bone during periodontal surgical procedures. The metal ions can be administered in polymeric microparticles, deformable films or microparticles embedded within deformable films. The metal ions are particularly microbiocidal to the bacterial pathogens that are the causative agents of periodontal disease.

12 Claims, 2 Drawing Sheets

U.S. PATENT DOCUMENTS

| | | | |
|---|---|---|---|
| 3,419,006 | 12/1968 | King | 128/268 |
| 3,639,575 | 2/1972 | Schmolka | 424/78 |
| 3,739,773 | 6/1973 | Schmitt et al. | 128/92 |
| 3,875,937 | 4/1975 | Schmitt et al. | 128/156 |
| 4,376,764 | 3/1983 | Schmolka | 424/78 |
| 4,476,590 | 10/1984 | Scales et al. | 128/156 |
| 4,559,223 | 12/1985 | Fox | 424/48 |
| 4,569,837 | 2/1986 | Suzuki et al. . | |
| 4,570,629 | 2/1986 | Widra | 128/156 |
| 4,588,400 | 5/1986 | Ring et al. | 604/304 |
| 4,685,883 | 8/1987 | Jernberg | 433/215 |
| 4,713,243 | 12/1987 | Schiraldi et al. . | |
| 4,728,323 | 3/1988 | Matson . | |
| 4,764,377 | 8/1988 | Goodson | 424/435 |
| 4,780,320 | 10/1988 | Baker | 424/493 |
| 4,808,402 | 2/1989 | Leibovich et al. | 424/423 |
| 4,846,165 | 7/1989 | Hare et al. . | |
| 4,847,049 | 7/1989 | Yamamoto | 422/24 |
| 4,892,736 | 1/1990 | Goodson | 424/435 |
| 4,906,670 | 3/1990 | Higashi et al. . | |
| 4,919,939 | 4/1990 | Baker | 424/473 |
| 4,933,182 | 6/1990 | Higashi et al. . | |
| 4,978,391 | 12/1990 | Jones . | |
| 4,981,693 | 1/1991 | Higashi et al. . | |
| 4,997,425 | 3/1991 | Shioya et al. | 604/304 |
| 5,009,898 | 4/1991 | Sakuma et al. | 424/618 |
| 5,019,096 | 5/1991 | Fox et al. | 623/1 |
| 5,023,082 | 6/1991 | Friedman et al. . | |
| 5,059,123 | 10/1991 | Jernberg | 433/215 |
| 5,077,049 | 12/1991 | Dunn et al. | 424/426 |
| 5,102,666 | 4/1992 | Acharya . | |
| 5,108,399 | 4/1992 | Eitenmuller et al. | 606/77 |
| 5,149,469 | 9/1992 | Komatsuzaki et al. | 264/28 |
| 5,197,882 | 3/1993 | Jernberg . | |
| 5,236,355 | 8/1993 | Brizzolara et al. | 433/80 |
| 5,260,066 | 11/1993 | Wood et al. | 424/447 |
| 5,298,015 | 3/1994 | Komatsuzaki et al. | 602/46 |
| 5,298,237 | 3/1994 | Fine | 424/49 |
| 5,326,567 | 7/1994 | Capelli | 424/405 |
| 5,340,581 | 8/1994 | Tseng et al. . | |
| 5,366,733 | 11/1994 | Brizzolara et al. . | |
| 5,387,419 | 2/1995 | Levy et al. | 424/422 |
| 5,468,489 | 11/1995 | Sakuma et al. | 424/49 |
| 5,534,288 | 7/1996 | Gruskin | 427/2.31 |
| 5,571,521 | 11/1996 | Lasker . | |
| 5,620,700 | 4/1997 | Berggren et al. | 424/435 |
| 5,622,498 | 4/1997 | Brizzolara et al. | 433/80 |
| 5,688,492 | 11/1997 | Galley et al. | 424/49 |
| 5,707,962 | 1/1998 | Chen et al. | 514/12 |
| 5,783,205 | 7/1998 | Berggren et al. | 424/435 |
| 5,955,097 | 9/1999 | Tapolsky et al. | 424/434 |

OTHER PUBLICATIONS

Dummett Postgraduate Medicine 49(1): 78–82 Systematic Significance of Oral Pigmentation and Discoloration, Jan. 1971.

Marshall et al Archives of Dermatology 113(8): 1077–1079 Systemic Argyria Secondary to Topical Silver Nitrate, Aug. 1977.

Lee et al Jl. of Dermatology 21(1): 50–53 Generalized Argyria After Habitual Use of AgNO3, Jan. 1994.

Jurizcka Haut Arzt 37(11): 628–631 Generalized Argyrosis, Nov. 1986.

MacIntire et al British Medical Journal 2(6154) : 1749–1750 Silver Poisoning Associated with an Antismoking Lozenge, Dec. 23–30, 1978.

Shelton et al British Medical Journal 1 (6158) : 267 Silver Poisoning Associated With an Antismoking Lozenge, Jan. 27, 1979.

Prescott et al Jl. Clin. Pathology 47(6): 556–557 Systemic Argyria, Jun. 1994.

Greene et al American Family Physician 36(6) : 151–154 Argyria, Dec. 1987.

Westhofen et al Areh. Oto–Rhino–caryngology 243(4)260–264 Generalized Argyrosis in Man, 1986.

Capoen et al Arhiu Franc. de Pediatrie 46(1): 49–50 Agryria in Children, Jan. 1989.

Zech et al Nouv. Press Medicine 2 (3) : 161–164 Generalized Argyria Silver mouthwash, Jan. 1973.

Williams, R., Medical Progress: Periodontal Disease, *N Engl J Med.*, 322:373–382 (1990).

Thibodeau, E. A., et al. "Inhibition and Killing of Oral Bacteria by Silver Ions Generated with Low Intensity Direct Current," *J Dent Res.*, 57(9–10): 922–926 (1978).

Russell, A.D. and Hugo, W.B., "Antimicrobial Activity and Action of Silver," *Prog Med Chem.*, 31: 351–370 (1994).

Howell, T.H., et al., "Sulfadiazines reduce gingivitis and plaque formation in beagle dogs," *J Clin Periodontol.*, 17: 734–737 (1990).

Howell, T.H., et al., "Sulfadiazines prevent plaque formation and gingivitis in beagles," *J Periodont Res.*, 25: 197–200 (1990).

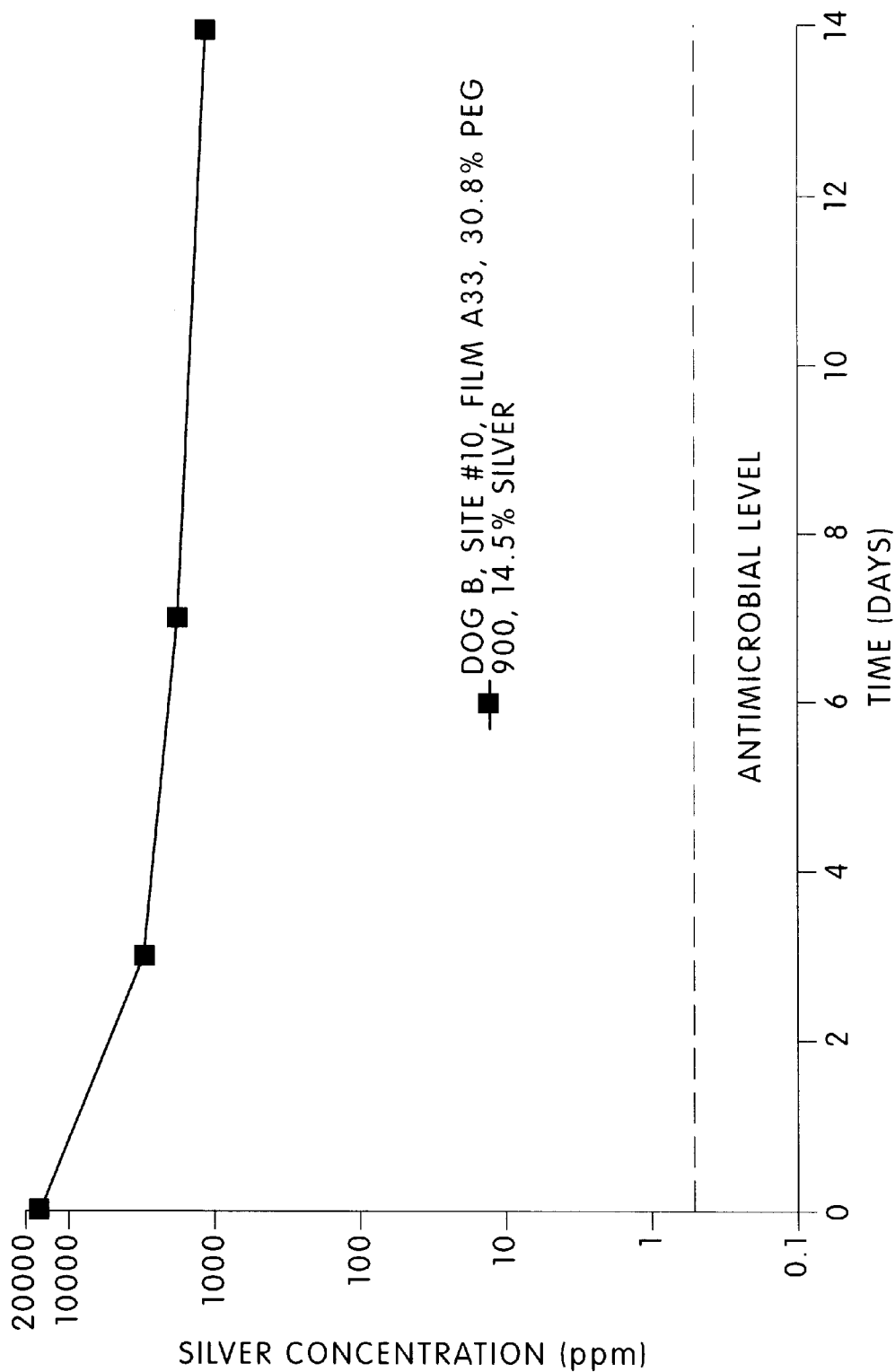

USE OF LOCALLY DELIVERED METAL IONS FOR TREATMENT OF PERIODONTAL DISEASE

BACKGROUND OF THE INVENTION

Continuing maladies that afflict man and other animals are tooth decay and tooth loss. Both of these afflictions have been subjected to much study and application of dental therapeutic measures with marginal success to date.

One aspect of dental therapy that has received attention is the understanding of and attempts at overcoming periodontal disease. Periodontal disease is a general term that encompasses diseases that affect the gingiva and diseases that affect the supporting connective tissue and alveolar bone which anchors the teeth in the jaws. A particular periodontal disease that can occur in individuals is periodontitis where connective tissue such as periodontal ligament tissue is lost, alveolar bone is resorbed and periodontal pockets are formed. In more advanced stages of such a periodontal disease, teeth become loosened and may eventually be lost. Periodontal diseases including periodontitis are caused by an accumulation of bacteria on the surface of the tooth and under the gingiva. Elimination of bacterial infection is key to the successful treatment of periodontal disease.

It has been known for some time that silver compounds exhibit antimicrobial activity. Currently, this knowledge is most often exploited in the treatment of burn wounds. There appear to have been limited attempts to use silver compounds in the treatment of periodontal disease. Silver sulfadiazine, when applied topically to the supragingival tooth surface in a gel base, has been shown both to prevent and to reduce gingival inflammation and plaque formation in beagle dogs (T. H. Howell et al., J. Periodontal Res. 25:197–200 (1990) and T. H. Howell et al., J. Clin. Periodontal. 17: 734–737 (1990)). However, these findings apparently have not been further pursued. Potential drawbacks to using silver compounds supragingivally in the treatment of periodontal disease are the staining of teeth and oral mucosa and the unpleasant taste that such treatment engenders. Thus, a potent, microbiocidally effective formulation that is locally applied subgingivally would provide a significant improvement in the treatment of periodontal disease.

SUMMARY OF THE INVENTION

The present invention pertains to methods for treating or preventing periodontal disease in individuals. These methods involve the administration of a microbiocidally effective amount of metal ions to the actual or, alternatively, a potential site of periodontal infection. The administration of these metal ions to the actual or potential site of periodontal infection causes a reduction in the number of viable microorganisms that are present at the actual or potential periodontal infection site. These microorganisms are the source of the periodontal disease from which relief is sought.

The present invention also pertains to delivery systems for use in treating or preventing periodontal disease in individuals. These delivery systems are solid or liquid formulations that release metal ions into an aqueous solution when the formulations are in contact with such solutions. In particular, the formulations are the releasable metal ions in a deformable or non-deformable solid carrier, in a gel carrier or in a combination of a solid and a gel carrier. These formulations, in preferred embodiments, are depositable into periodontal pockets and/or adhereable to teeth at the root surface and/or to the gingival tissue below the gum line.

Advantages of the present invention are the manner of treatment and the efficacy of treating periodontal disease that is provided by the administration of metal ions to the actual or potential sites of periodontal infection. With the present invention, the administered metal ions are particularly potent in their microbiocidal activity against the microorganisms that are the causative agents of periodontal infection.

BRIEF DESCRIPTION OF THE DRAWINGS

FIG. 2 is a graphical representation of the amount of silver ions that is released over time from a polymeric film made up of poly(lactic glycolic acid)(PLGA) with 15.4 wt % polyethylene glycol (PEG) and 14.5 wt % silver nitrate that was placed in a periodontal pocket.

Figure 1:
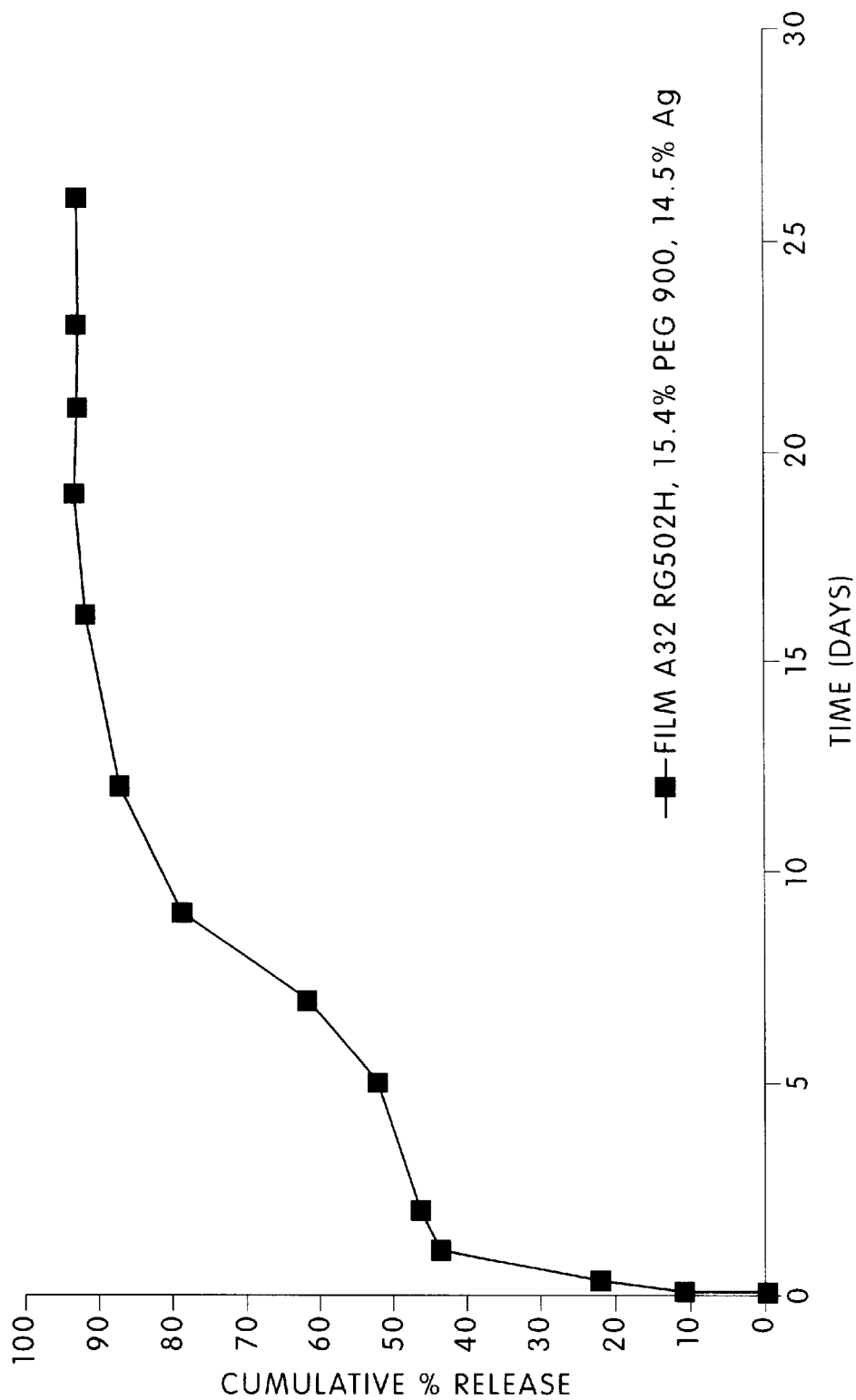
FIG. 1 is a graphical representation of the cumulative release of silver ions from a polymeric film made up of poly(lactic glycolic acid)(PLGA) with 15.4 wt % polyethylene glycol (PEG) and 14.5 wt % silver nitrate into an aqueous bathing medium.

The file of this patent contains at least one drawing executed in color. Copies of this patent with color drawing(s) will be provided by the Patent and Trademark Office upon request and payment of the necessary fee.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

This invention, in one of its aspects, pertains to methods for treating or for preventing periodontal disease in an individual, particularly in a human being. Periodontal disease is typically manifested as an inflammation of the gingival tissue often coupled with a loss of supporting structural tissue surrounding the roots of the teeth in the individual. A particularly appropriate form of periodontal disease that is treatable by the present invention is periodontitis which is manifested as the loss of alveolar bone and of connective tissue that attaches the tooth root surface and cementum to the alveolar bone. This loss of tissue results in the formation of pronounced periodontal pockets. Periodontitis is defined as the existence of periodontal pocket depths of at least 3 millimeters (mm) as assessed by mechanical probing. The present invention can be used to alleviate the periodontitis disease state for periodontal pockets of 3–6 mm and even when the periodontal pockets reach a depth greater than 6 mm.

Periodontal disease, including periodontitis, is strongly correlated with the presence of certain microorganisms, particularly specific bacteria, that reside in the periodontal region of the mouth. These microorganisms or their metabolic products have been implicated as the causative source of periodontal disease. Specific microorganisms that have been suggested as causative agents of periodontal disease are *Actinobacillus actinomycetemcomitans, Bacteroides forsythus, Campylobacter rectus, Eikenella corrodens, Fusobacterium nucleatum ss vincentii, Peptostreptococcus micros, Porphyromonas gingivalis, Prevotella denticola, Prevotella intermedia, Prevotella nigrescens, Streptococcus intermedius, Treponema denticola, Campylobacter gracilis* and *Actinomyces viscosus*. Mixtures of two or more microbial species may be present and causing, either individually or synergistically, periodontal disease.

The formulations of the present invention are effective as microbiocides against the periodontal disease-causing microorganisms. In particular, the formulations of the present invention are effective against the aforementioned listed microbial species, either as individual species or as combinations of species. These formulations kill the microorganisms, thereby diminishing the number of viable microbial cells and, thereby, their periodontal disease effect. Maximum efficacy is achieved when all the periodontal disease-causing microorganisms are eradicated.

In order to achieve microbiocidal action, a microbiocidally effective amount of the active agent in the formulations of the invention must be administered to the host individual. This amount is considered to be the quantity of active agent that causes a decrease in number of viable periodontal disease-causing microorganisms when appropriately administered to the host individual.

To achieve efficacy, the formulations of the present invention are preferentially administered to the anatomic sites where periodontal disease, e.g., periodontitis, occurs. The formulations can be administered elsewhere to the body of the host individual but better efficacy is achieved when the formulations are directly administered to the sites where periodontal disease exists or where the disease may reoccur, i.e., to periodontal pockets or to exposed tooth roots and/or alveolar bone that are exposed during periodontal surgical procedures to repair periodontal tissue that has degenerated as a result of periodontal disease; in particular, to periodontal sites where periodontal surgical procedures are being performed to ameliorate periodontitis. These anatomic sites include the periodontal pockets, the interfacial region that exists where the tooth surface and the gingiva meet and surface of the tooth root below the gum line (i.e., below the cementoenamel junction). These sites for administration of the formulations of the invention are the anatomic regions where the microbial flora reside that cause periodontal disease. Application of the formulations of the invention to these sites is the most efficient means to supply a microbiocidally effective amount of the active agent to these microbial flora and thereby achieve adequate microbiocidal activity of the active agent against the periodontal disease-causing microorganisms.

The active agents of the present invention that are the microbiocides of the periodontal disease-causing microorganisms are metal ions. Metal ions that are efficacious as microbiocides against periodontal disease-causing microorganisms include silver ions, zinc ions, copper ions, iron ions and nickel ions. Combinations of these ion species can also be used.

A particularly preferred active agent is silver ions. In the formulations of the present invention, the silver ions are initially in chemical combination with an anionic species to form a salt or with a complexing substance to form a chemical complex. Thus, the silver ions are inserted in the formulations of the present invention as, for example, silver acetate, silver bromate, silver chlorate, silver perchlorate, silver chlorite, silver fluoride, silver lactate, silver permanganate, silver protein, silver nitrate, silver nitrite, silver sulfadiazine, silver sulfate or combinations of these chemical compounds and complexes. Of these chemical compounds and complexes, silver nitrate, silver chlorate, silver perchlorate and silver fluoride are preferred.

From the chemical combination or complex in the formulations of the present invention, the metal, e.g., silver, is released as metal ions. As previously mentioned, these ions are the microbiocidal agents. They are normally released, following administration of the formulations of the invention, into an aqueous medium. They are released, following the preferential administration to the anatomic sites where periodontal disease occurs, into the aqueous medium that also contains the periodontal disease-causing microorganisms. When such preferential administration of the formulations is performed, the aqueous medium into which the metal ions are released is either saliva or crevicular fluid that occupies the gingival crevice and periodontal pockets. It has been determined that the concentration of metal, e.g., silver, ions that is microbiocidal to the periodontal disease-causing microorganisms can be as low as 0.5 parts per million (ppm) (500 ng/ml) in the aqueous environment containing these microorganisms. Higher concentrations are also microbiocidal, of course, but this finding indicates that minimal amounts of the active metal agents can be administered with an expectation of microbiocidal activity.

In addition, the finding that low concentrations of metal ions are effective in their microbiocidal activity against periodontal disease-causing microorganisms indicates that slow, sustained release of the metal ions from the formulations of the present invention will be efficacious in maintaining a microbiocidal concentration of the metal ions in the aqueous medium that is in contact with the periodontal disease-causing microorganisms. The metal ions can be slowly released from the formulations of the present invention for periods of time up to four weeks in duration. Slow release of the metal ions from the formulations of the present invention up to 12 weeks is achievable, particularly because relatively low concentrations of the metal ions are microbiocidal. When the formulations of this invention are administered to the anatomic sites where periodontal disease occurs, slow release of the metal ions from the formulations is usually preferred because repeated administrations of the formulations is inconvenient and somewhat time consuming. Single administrations are particularly important when the formulations are administered during periodontal surgical procedures because the initially exposed tooth roots and/or alveolar bone are closed at the end of the procedures by suturing the gingival flaps. For these reasons, repetitive administrations are possible but not preferable.

The formulations of the present invention that can be administered to the host can be any one of many forms. For example, the formulation can be a liquid solution containing the metal ions, usually in an aforementioned chemical combination or complex. In this formulation the metal ions, e.g., in a chemical combination or complex, are dissolved or suspended in the liquid carrier for ease of eventual administration. This liquid solution or suspension can easily be administered into the periodontal pocket or to the exposed tooth roots and/or alveolar bone during surgical procedures.

Another formulation of the present invention is a gel containing the metal ions. The metal ions, again usually in chemical combination or complex as previously described, are thoroughly mixed with the gel carrier material. Alternatively, the metal ions are placed in a solid carrier such as microparticles, as will be subsequently described, which are then placed in the gel carrier material. The gel carrier can be placed at the appropriate anatomic site in the host individual such as in the periodontal pockets or on the exposed tooth roots and/or alveolar bone during surgical procedures. The metal ions are released from the gel, or from the microparticles embedded within the gel, into the aqueous medium that is in contact with the periodontal disease-causing microorganisms. The metal ion release can be slow and can result from biodegradation of the gel and/or solid carrier material in the aqueous medium or from enzymatic activity of constitutive enzymes normally found in the aqueous medium.

Another formulation of the present invention is a solid carrier such as a tablet, capsule, microparticles, film, wafer, or chip containing the metal ions. The metal ions, again usually in chemical combination or complex as previously described, are thoroughly mixed with the inert solid carrier material and thereby incorporated within the confines of the carrier. This carrier can then be locally administered to the individual. When the solid carrier is in the form of microparticles, these microparticles can be suspended in a suitable liquid or gel medium for administration to the host. For example, the microparticle suspension can be inserted directly into the periodontal pockets. The metal ions are released from the solid carrier, e.g., by slow release, when the solid carrier is placed in the aqueous medium. The released metal ions then microbiocidally act on the periodontal disease-causing microorganisms that are in contact with this medium. The metal ion release usually occurs by diffusion and/or dissolution from and/or degradation of the solid carrier material in the aqueous medium. The solid carrier degradation can be caused or enhanced by substances, such as enzymes, that naturally exist in the aqueous medium.

A particular solid formulation of the present invention is a film containing the metal ions. The metal ions, again usually in chemical combination or complex as previously described, are incorporated in the precursor carrier material as the film is formed. The film can be non-deformable or, more preferably, deformable at room and human body temperature (20° C. to 37° C.). The deformable film can be subgingivally placed in the mouth of the host individual. In particular, the deformable film can be placed in periodontal pockets. Alternatively, the deformable film can be placed adjacent to exposed tooth roots and/or alveolar bone during periodontal surgical procedures. Such placement allows ample contact between the film and the anatomic sites containing or potentially containing the periodontal disease-causing microorganisms. The metal ions are released from the film into the aqueous medium that is in contact with the film. This release can be slow and aided or resulting from biodegradation of the film in the aqueous medium.

Solid carriers, such as microparticles, can be the repository of the metal ions, as previously described, which can be placed in the film carrier. This aspect of the invention is similar to that previously described for solid carriers placed in a gel. The film containing the solid carriers can be deformed for suitable placement in periodontal pockets or adjacent to exposed tooth roots and/or alveolar bone during surgical procedures, particularly when the film is deformable in the 20° C. to 37° C. temperature range. Again, slow release can occur, particularly as the film and/or solid carrier is biodegraded.

The solid carrier, gel and/or film of the formulations of the present invention can be made of one or more polymeric materials. Such polymeric materials are preferred carriers for the active agents of the present invention. These polymeric materials can readily be formed to contain the metal ions of the invention which are initially in a chemical combination or complex. The polymeric materials can also be biodegradable. Preferable polymers from which the final polymeric materials are made include gelatin, polyethylene glycol, polypropylene glycol, copolymers of ethylene oxide and propylene oxide, copolymers of polyethylene glycol and polypropylene glycol, polytetramethylene glycol, polyether urethane, hydroxyethyl cellulose, hydroxypropylmethyl cellulose, alginate, collagen, polylactide, poly(lactide-co-glycolide), calcium polycarbophil, polyethylmethacrylate, cellulose acetate, ethyl cellulose, propylene glycol, polyacrylic acid, crosslinked polyacrylic acid, Carbopol™, hydroxyethyl methacrylate/methyl methacrylate copolymer, silicon/ethyl cellulose/polyethylene glycol, hydroxypropyl cellulose, polyethylene oxide, urethane polyacrylate, polystyrene, polysulfone, polycarbonate, polyorthoesters, polyanhydrides, poly(amino acids), partially and completely hydrolyzed alkylene-vinyl acetate copolymers, polyvinyl chloride, polymers of polyvinyl acetate, polyvinyl alkyl ethers, polyvinyl fluoride, Silicone™, polyurethane, polyamide, styrene acrylonitrile copolymers, poly(ethylene oxide), poly(ethylene terephthalate), poly(alkylenes), poly(vinyl imidazole), poly(esters) and combinations of two or more of these polymers. The combinations of polymeric materials can be mixtures of two or more polymers such that the signature identity of an individual polymer cannot be discerned in the mixture. Alternatively, the combinations of polymeric materials can be one polymer in a particular form, such as a solid microparticle, embedded within another polymer in another form, such as a gel or a film.

In particularly preferred embodiments, the polymeric material is a combination of polyethylene glycol and/or block copolymers of poly(ethylene) oxide and poly(propylene) oxide with poly(lactide-co-glycolide) also known as poly(lactic glycolic acid) (PLGA). This combination of polymeric materials can be either in the form of a deformable film or as microparticles embedded within a deformable film. The poly(ethylene) glycol (PEG) can have a variety of molecular weights so a mixture of poly(ethylene) glycol (PEGs) can be present. The PEGs and the block copolymers of poly(ethylene) oxide and poly(propylene) oxide (Pluronics™) can act as plasticizers for the PLGA when a film is to be formed. Such a combination yields films with desirable physical properties, such as deformability at usable temperatures, and metal release profiles, such as slow release of two weeks or more for the microbiocidal metal ions. For example, a PLGA of lower molecular weight (e.g., 12,000 Daltons) and with terminal carboxyl groups yield a desired delivery time for the antimicrobial metals of about one month. Higher molecular weight and/or end-capped PLGA can be used if other release profiles are desired. In the deformable film form, the desirable ratio of poly(lactid-co-glycolide) to polyethylene glycol and/or the block copolymers of poly(ethylene) oxide and poly(propylene) oxide can vary from about 10:1 to about 1:1. The desirable ratio of PEG to Pluronic™ in such deformable films that incorporate PLGA ranges from about 10:1 to 1:10.

The invention is further illustrated by the following specific examples. These examples should not be construed as limiting the invention in any way.

EXAMPLE 1

Formation of Polymeric Carriers Containing Antimicrobial Metal Ions

Poly(lactic glycolic acid) (PLGA) was used as the bioerodible matrix for delivering antimicrobial metals. The amount of PLGA (MW 12,000, 50:50 lactic:glycolic, Boehringer Ingelheim Chemicals, RG502H) typically incorporated into the matrix film ranged from 64 to 86% (w/w). Plasticizers used were PEG alone, Pluronic™ alone, or a combination of PEG and Pluronic™. The PEGs that were used ranged in molecular weight from 900 to 4500 and typically yielded very flexible films, regardless of the molecular weight used. A variety of Pluronics™ were also incorporated, including L101, L122, P65, P105, F68, F87, and F127. Pluronics™ alone typically yielded films that were significantly more brittle than films with approximately equal percentages of PEG.

It was found that the most desirable physical properties of the matrix film were obtained when a combination of PEG and Pluronic™ was used. The ratio of PEG to Pluronic™ incorporated into the PLGA ranged from 90:10 to 50:50.

The PLGA films were prepared either by solvent casting or melt casting. To prepare the films by solvent casting, the PLGA was dissolved into a 3:1 organic solvent mixture of acetone/acetonitrile with varying amounts of PEG, Pluronic™, or a combination of these plasticizers. Next, the appropriate amount of a metal salt (e.g., $AgNO_3$) was dissolved in the solution. The polymer/salt solution was poured onto Teflon plates, and the solvent was allowed to evaporate from the solution at room temperature and pressure. Films prepared by solvent casting were typically clear and homogenous.

An alternative, more rapid method of preparing the films was to melt cast them onto Teflon plates. The polymer solution was prepared as previously described for the solvent casting method, and the solution was poured onto Teflon plates. The solvent was then evaporated from the solution by subjecting it to a vacuum (~30 in. Hg) for 1.5 hours. The resulting homogenous solid was then rolled into a sphere and placed between two Teflon-coated plates. The polymer and plates were placed into an oven and heated to temperatures up to 110° C. Under the influence of the heat, the polymer became quite soft and was pressed into a thin film after heating for an hour. The thickness of the film was controlled by using spacers between the plates during the pressing procedure.

EXAMPLE 2

Placement of Antimicrobial Metal Containing Formulations at Periodontal Sites in Dogs Two mature female Beagle dogs (Harlan Inc.) were used in this study. One week prior to baseline the dogs were anesthetized and received a complete periodontal examination and supragingival tooth cleaning with ultrasonics and dental curettes. The dogs were housed in an approved animal care facility throughout the course of the study.

The baseline visit consisted of two gingival crevicular fluid (GCF) samplings and placement of a silver-containing film delivery system into periodontal pockets. One GCF sample was taken prior to drug delivery and another at approximately 10 minutes following drug delivery. The GCF sampling technique consisted of isolation and drying of the test tooth and associated periodontium followed by the insertion of a filter paper strip into the periodontal pocket for 20 seconds. The volume of GCF on the paper strip was assessed visually and recorded. The test sites consisted of sites that probed 5 mm or greater at the time of the periodontal exam. There were four test sites in Dog A and eight test sites in Dog B. Following the baseline and ten minutes GCF sample, each site was covered with Octyldent™ adhesive (dressing) and the dog returned to the animal care facility.

Gingival crevicular fluid samples were obtained from all sites at 3, 7 and 14 days post baseline. Prior to sampling the dressing was trimmed to allow for access to the opening of the periodontal pocket. Sampling was done as previously described. Each site was also indexed for presence or absence of both dressing and drug delivery system retention. Following the GCF sampling, the Octyldent™ adhesive was reapplied to each site that was initially treated. Four sites in Dog A received the silver-containing film. In Dog B, eight sites had silver-containing film inserted. In each instance, the film was initially inserted into the periodontal pocket and then compacted in place in the pocket.

EXAMPLE 3

Release Profiles for Antimicrobial Metal Ions in Polymeric Carrier Formulations

In vitro and in vivo release was performed using films prepared as described in Example 1 above. For the in vitro release studies, duplicate strips of films weighing 20 mg were cut from the bulk film and placed in 1.5 mL centrifuge vials. One mL of deionized water was added to the vial, and the vial was closed and placed on its side in a 37° C. incubator. To determine the release of silver at various time points, a 500 µL sample was extracted, diluted to 10 mL, and analyzed for free silver using a silver ion selective electrode (ISE). A 500 µL aliquot of deionized water was used to refill the sample vial and the vial was placed back in the incubator until the next measurement was taken. Typical in vitro and dog in vivo release curves are shown in FIGS. 1 and 2, respectively. There is typically an initial release burst within the first two days. Following the release burst, the metal ions are released more slowly as the polymer is hydrated and begins to degrade. In FIG. 1, the initial release burst of 44% is followed by a more gradual release to Day 16 as the polymer degrades. In FIG. 2, very high levels of silver remain in the periodontal pocket after 14 days, and it is expected that antimicrobial levels remain even after an additional one to two weeks.

EXAMPLE 4

Antimicrobial Effect of Metal Ions on Oral Bacteria

Bacteria initially cultured anaerobically in liquid or on plates were suspended in phosphate buffered saline and combined with an equal volume of the same buffer +/- the antimicrobial agent. The resulting mixtures, which contained $10^4$ or $10^5$ cfu/ml were incubated anaerobically for 1 hour prior to dilution and plating. The plated incubation mixtures were incubated anaerobically at 35° C. until colonies developed.

Percent killing of the bacteria was determined by comparison of control incubations to those containing the antimicrobial agents. Table 1 shows the % killing that occurred at different concentrations (parts per million or ppm) of the active agent. This Table also shows the reduction in viable microorganisms on a logarithmic scale at the listed concentrations of active agent.

TABLE 1

| BACTERIUM | AGENT | % KILLING | LOG RED'n VIABILITY |
|---|---|---|---|
| C. rectus 371 | $AgNO_3$ | 100%; 0.5 ppm | 4.11 |
| | | 100%; 0.05 ppm | 4.11 |
| B. forsythus 338 | $AgNO_3$ | 100%; 0.5 ppm | 3.2 |
| | | 14–24%; 0.05 ppm | 0.08 |
| B. forsythus 338 | $AgNO_3$ | 100%; 0.5 ppm | 4.16 |
| | | 50%; 0.05 ppm | 1.59 |

TABLE 1-continued

| BACTERIUM | AGENT | % KILLING | LOG RED'n VIABILITY |
|---|---|---|---|
| F. nucleatum ss vincentii | $AgNO_3$ | 100%; 0.5 ppm | 2.08 |
| F. nucleatum ss vincentii | $AgNO_3$ | 100%; 0.5 ppm 97%; 0.05 ppm | 3.77 1.58 |
| E. corrodens 23834 | $AgNO_3$ | 100%; 5 ppm 84%; 0.5 ppm | 3.0 0.81 |
| E. corrodens 23834 | $AgNO_3$ | 100%; 5 ppm >99%; 0.5 ppm | 3.38 3.08 |
| E. corrodens #558 | $AgNO_3$ $CuCl_2$ | 100%/>99%; 5/0.5 ppm 78%/58%; 5/0.5 ppm | 4.29/3.89 <<1 |
| C. gracilis #1084 | $AgNO_3$ $CuCl_2$ | 100%; 5/0.5 ppm 83%/80%; 5/0.5 ppm | 3.36/3.68 0.77/0.71 |
| P. gingivalis A7A1-28 | $AgNO_3$ | 100%; 0.05 ppm >99–100%; 0.005 ppm | 3.18 1.3 |
| P. gingivalis A7A1-28 | $AgSO_4$ | 100%; 0.05 ppm 37–67%; 0.005 ppm | 2.4 0.18 |
| P. gingivalis A7A1-28 | $CuCl_2$ | 100%; 25–5–0.5/ 5–0.5 ppm 99%; 0.005 ppm | 4.18/4.03 1.9 |
| P. gingivalis A7A1-28 | $ZnCl_2$ | | No Killing |
| S. sobrinus 6175 | $AgNO_3$ | 50/5/0.5 ppm | No Killing |
| S. sobrinus 6175 | $AgNO_3$ | 50/5/0.5 ppm | No Killing |
| S. sobrinus DS-1 | $AgNO_3$ | 0/39/16%; 25/5/0.5 ppm | No Killing |
| A. viscosus | $AgNO_3$ | 100%/100%/>99%; 25/5/0.5 ppm | 3.68/2.73/2.75 |
| S. mitis JK 195 | $AgNO_3$ | 30–39%; 50/5/0.5 ppm | 0.32/0.32/0.32 |
| S. mitis JK 195 | $CuCl_2$ | 100%; 50/5 ppm 40%; 0.5 ppm | 4.14/3.08 0.3 |
| S. mitis JK 195 | $AgNO_3$ | 40–45%; 50/5/0.5 ppm | 0.25/0.25/0.25 |
| S. mitis JK 195 | $CuCl_2$ | 99%; 50/5 ppm 20%; 0.5 ppm | 4.26/4.26 0.18 |
| S. mutans SJ32 | $AgNO_3$ | 50/5/0.5 ppm | No Killing |
| S. mutans SJ32 | $CuCl_2$ | 100%; 50/5 ppm 99%; 0.5 ppm | 3.53/3.53 2.53 |
| S. mutans SJ32 | $AgNO_3$ | 99%; 50 ppm 5/0.5 ppm | 2.53 No Killing |
| S. mutans SJ32 | $CuCl_2$ | 100%; 50/5 ppm/ 0.5 ppm | 3.54/3.54/3.54 |
| P. denticola | $AgNO_3$ | 100%; 0.5 ppm | 4.07/3.83 |
| A. actinomycetemcomitans | $AgNO_3$ | >99%; 0.5 ppm | 2.95 |
| A. actinomycetemcomitans | $AgNO_3$ | 100%; 0.5 ppm | 3.90 |

The results shown in Table 1 demonstrate that the metal ion agents are potent microbiocidal substances. In particular, silver ions cause at least a three log reduction of viable cells for P. gingivalis, C. rectus, B. forsythus, E. corrodens, F. nucleatum ss vincentii, and C. gracilis at concentrations of 0.5 ppm or lower. A three log reduction of viable P. intermedia cells occurs when the concentration of silver ions is 0.05 ppm or lower. Copper ions cause at least a three log reduction of viable P. gingivalis cells at concentrations of 0.5 ppm or lower.

While the microbiocidal activity of silver ions against S.sobrinus, S.mitis and S.mutans is apparently relatively low, these results do not detract from the inventive use of silver ions in treating periodontal disease since these microorganisms are not considered to be periodontal disease-causing pathogens. In fact, these results demonstrate the enhanced microbe selectivity that silver ions possess for eradicating periodontal disease-causing pathogens.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating or preventing periodontitis in an individual comprising:
    administrating to a periodontal pocket or oral surgical site of said individual a polymeric film containing silver nitrate to deliver silver ion to said periodontal pocket or surgical site sufficient to exert an antimicrobial effect for at least fourteen days at or adjacent to said pocket or site.

2. The method of claim 1, wherein the polymeric film further comprises one or more polymeric materials selected from the group consisting of gelatin, polyethylene glycol, polypropylene glycol, polytetramethylene glycol, copolymers of ethylene oxide and propylene oxide, copolymers of polyethylene glycol and polypropylene glycol, polyether urethane, hydroxyethyl cellulose, hydroxypropylmethyl cellulose, alginate, collagen, polyethylmethacrylate, cellulose acetate, ethyl cellulose, propylene glycol, polyacrylic acid, crosslinked polyacrylic acid, propylene glycol, Carbopol™, hydroxyethyl methacrylate/methyl methacrylate copolymer, silicon/ethyl cellulose/polyethylene glycol, hydroxypropyl cellulose, polyethylene oxide, urethane polyacrylate, polystyrene, polysulfone, polycarbonate, polyorthoesters, polyanhydrides, poly(amino acids), partially and completely hydrolyzed alkylene-vinyl acetate copolymers, polyvinyl chloride, polymers of polyvinyl acetate, polyvinyl alkyl ethers, polyvinyl fluoride, polyurethane, polyamide, styrene acrylonitrile copolymers, poly(ethylene oxide), poly(ethylene terephthalate), poly(alkylenes), poly(vinyl imidazole), poly(esters) and combinations of two or more of these polymers.

3. The method of claim 2, wherein the polymeric film is biodegradable.

4. The method of claim 1, wherein the polymeric film is comprised of poly(lactide-co-glycolide).

5. The method of claim 1, wherein the polymeric film is comprised of a combination of polyethylene glycol and poly(lactide-co-glycolide).

6. The method of claim 1, wherein the film is deformable at room and body temperature.

7. The method of claim 2, wherein the polymeric film comprises a plasticizer.

8. The method of claim 1, wherein the concentration of silver ion in an aqueous environment of the pocket or site is in the range of 0.1 to 5.0 ppm.

9. The method of claim 8, wherein the aqueous environment is saliva or crevicular fluid.

10. The method of claim 1, wherein the polymeric film is formulated to release an antimicrobial level of silver ions for greater than or equal to 4 weeks.

11. The method of claim 1, wherein the polymeric film is formulated to release an antimicrobial level of silver ions for up to 12 weeks.

12. The method of claim 1, wherein periodontal disease-causing microorganisms are members of microbe species selected from the group consisting of *Actinobacillus actinomycetemcomitans, Bacteroides forsythus, Camphylobacter rectus, Eikenella corrodens, Fusobacterium nucleatus ss vincentii, Peptostreptococcus micros, Porphyromonas gingivalis, Prevotella denticola, Prevotella intermedia, Prevotella nigrescens, Streptococcus intermedius, Treponema denticola, Campylobacter gracilis, Actinomyces viscosus* and mixtures of two or more of these species.

* * * * *